(12) United States Patent
Sahoo et al.

(10) Patent No.: US 12,305,154 B2
(45) Date of Patent: May 20, 2025

(54) PROCESS FOR MICROBIAL SYNTHESIS AND AN APPARATUS THEREOF

(71) Applicant: Indian Oil Corporation Limited, Mumbai (IN)

(72) Inventors: Prakash Chandra Sahoo, Faridabad (IN); Manoj Kumar, Faridabad (IN); Ravi Prakash Gupta, Faridabad (IN); Suresh Kumar Puri, Faridabad (IN); Deepak Saxena, Faridabad (IN); Sankara Sri Venkata Ramakumar, Faridabad (IN)

(73) Assignee: Indian Oil Corporation Limited, Mumbai (IN)

( * ) Notice: Subject to any disclaimer, the term of this patent is extended or adjusted under 35 U.S.C. 154(b) by 862 days.

(21) Appl. No.: 17/448,801

(22) Filed: Sep. 24, 2021

(65) Prior Publication Data

US 2022/0098537 A1  Mar. 31, 2022

(30) Foreign Application Priority Data

Sep. 25, 2020 (IN) .............................. 202021041728

(51) Int. Cl.
  *C12M 1/00* (2006.01)
  *C12M 1/02* (2006.01)
  *C12N 1/20* (2006.01)
  *C12P 7/06* (2006.01)
  (Continued)

(52) U.S. Cl.
  CPC ............ *C12M 29/06* (2013.01); *C12M 31/00* (2013.01); *C12M 41/24* (2013.01); *C12N 1/20* (2013.01); *C12N 2500/05* (2013.01); *C12N 2500/30* (2013.01); *C12N 2529/00* (2013.01); *C12R 2001/425* (2021.05)

(58) Field of Classification Search
  None
  See application file for complete search history.

(56) References Cited

U.S. PATENT DOCUMENTS

| 7,531,350 B2 | 5/2009 | Shiau |
| 2009/0035848 A1* | 2/2009 | Hickey ................. C12M 33/14 435/296.1 |

(Continued)

FOREIGN PATENT DOCUMENTS

| CA | 1179616 A | 12/1984 |
| CN | 110656027 A | 1/2020 |

OTHER PUBLICATIONS

Chun-Zhao Liu et al, "Production of artemisinin by shoot cultures of *Artemisia annua* L. in a modified inner-loop mist bioreactor", Plant Science, 1998, pp. 211-217, vol. 135.

(Continued)

*Primary Examiner* — Neil N Turk
(74) *Attorney, Agent, or Firm* — Workman Nydegger (57) ABSTRACT

The present invention relates to a process for microbial synthesis process having less water consumption and yielding desired product profile. More particularly, the present invention relates to an improved process of microbial synthesis using ultra fine nutrient mist in a specially designed biofilm-bioreactor under controlled conditions. The present invention also relates to an apparatus for microbial synthesis and preparation of optimized biofilm for continuous product formation.

17 Claims, 3 Drawing Sheets

(51) Int. Cl.
  *C12P 7/16* (2006.01)
  *C12R 1/425* (2006.01)

(56) References Cited

U.S. PATENT DOCUMENTS

2024/0237217 A9* 7/2024 Jeong ............... H05K 1/181
2024/0247217 A1* 7/2024 Lawton ............. C12M 31/10

OTHER PUBLICATIONS

Alireza Valdiani et al., "Bioreactor-based advances in plant tissue and cell culture: challenges and prospects", Critical Reviews in Biotechnology, 2018, DOI: 10.1080/07388551.2018.1489778.
D.M. Goeres et al., "Design and fabrication of biofilm reactors", Recent Trends in Biofilm Science and Technology, 2020, pp. 71-88, https://doi.org/10.1016/B978-0-12-819497-3.00003-9.

* cited by examiner

PROCESS FOR MICROBIAL SYNTHESIS AND AN APPARATUS THEREOF

FIELD OF THE INVENTION

The present invention relates to a process of microbial synthesis having less water consumption and yielding desired product profile. More particularly, the present invention provides an improved process for microbial synthesis using ultra fine nutrient mist in a specially designed biofilm-bioreactor under controlled conditions. The present invention also relates to an apparatus for microbial synthesis and preparation of optimized biofilm for continuous product formation.

BACKGROUND OF THE INVENTION

Industrial bioprocessing has been used for green and sustainable production of chemicals and fuels. For industrial bioprocessing water is an essential commodity. Industrial bioprocessing processes such as fermentation and cell-culture processes are extremely water-intensive. For instance, these processes require over 10,000 L of water for every kilogram of product.

CA1179616A describes a method for preparation of inocula with low water activity and improved resistance to thermal factors and rehydration. This invention relates to an inoculum preparation process with low water activity with a long viability and improved resistance to temperature and rehydration. As per the invention, after inclusion of microorganism in a polymeric gel is lowered and maintained the activity of water in the inoculum below 0, 1 and that the rehydration is facilitated by the presence of the gel and of the hydrocarbon source present in the medium. This process applies to the pre-coating of seeds and soil inoculation. However, the process is a continuous bioprocessing method. The resulted microbes are not stable on the polymeric material and may be affected with feed and product concentration. Nutrients for microbial growth have to be supplied manually, which may contaminate the microbial culture.

CN 110656027 A discloses a gas-liquid reverse transmission biomembrane reactor for preparing ethanol by fermenting waste gas $CO/CO_2$ comprises an upper part of a shell and a lower part of the shell which are connected through a flange, wherein the top of the upper part of the shell is provided with an exhaust hole. The invention utilizes the biomembrane reactor for gas-liquid reverse transmission to realize the utilization $CO/CO_2$. Ethanol is prepared by fermenting the waste gas.

U.S. Pat. No. 7,531,350B2 discloses a simple and portable mist bioreactor showing substantial growth rate and increased product yields. The document discloses that nutrient mists are uniformly distributed on the explants in a short time period. However, the document fails to disclose the preparation of biofilm for continuous product formation.

Liu et al. relates to modified inner-loop ultrasonic nutrient mist bioreactor with three stainless steel meshes used to form culture shoots of *Artemisia annua* L. to produce artemisinin.

Valdiani et al. describes stability, operational ease, improved nutrient uptake capacity, time- and cost-effectiveness, and large quantities of biomass production, that make bioreactors suitable alternatives to conventional plant tissue and cell culture (PTCC) methods.

Goeres et al. describes process used to design and fabricate a biofilm reactor with the goal of generating a commercial product.

Although, available literature provides several methods for bioprocessing, however, the methods available face several challenges and drawbacks such as very high requirement of water for microbe cultivation and fermentation, requirement of autoclaved water/high purified water for bioprocessing, large quantities of water used for equipment Clean in Place (CIP), lack of an efficient provision for optimized nutrient supply for microbial growth, high cost of down-streaming separation of synthesized products. Thus, there is a need in the art to develop a bioprocessing process with less water consumption and having low product separation cost.

SUMMARY OF THE INVENTION

In an aspect of the present invention, there is provided an improved process for microbial synthesis, the process comprising the steps of:

(a) inoculating an electro active microbe in a nutrient mist medium in a mist generating and conditioning chamber;

(b) adding a mist conditioning agent in the range of 50-70 ppm to the nutrient mist medium of step (a); mechanically mixing solutions of (a) and (b) in the chamber to form a homogeneous mixture and adding a bacterio-supramolecular self-assembly agent to the solution to obtain an ultra-fine mist;

(c) passing the obtained mist through a UV chamber for a duration of 2-5 seconds and sparging nitrogen gas or dry air to the mist in a mist bioreactor; wherein the ratio of mist and nitrogen gas is 1:2;

(d) layering the microbe on a biofilm support in the bioreactor to obtain a stable biofilm and passing controlled feed and collecting product in a product collection and separation chamber, wherein the microbe is added in the mist bioreactor along with a moisture indicator and ZnSe quantum dots in a concentration ranging from 100-500 nM.

In an embodiment of the present invention, there is provided a process for microbial synthesis, wherein the electro active microbe is selected from the group consisting of *Enterobacter aerogenes* MTCC 25016, *Serratia* sp. MTCC 25017, *Shewanella* sp. MTCC 25020 and *Alcaligenes* sp. MTCC 25022.

In another embodiment of the present invention, there is provided a process for microbial synthesis, wherein the bacterio-supramolecular self-assembly agent is dioleoylphosphatydic acid.

In another embodiment of the present invention, there is provided a process for microbial synthesis, wherein the moisture indicator is selected from $CuCl_2$/silica Gel, porphyrin/$MgCl_2$/silica Gel, and Fe-hydroxy complexes/silica gel.

In yet another embodiment of the present invention, there is provided a process for microbial synthesis, wherein the nutrient mist medium is selected from complex dextrose based media, sea water media, domestic wastewater, municipal wastewater, industrial wastewater, surface runoff wastewater, soil extract media, or natural water; a defined medium, or a selective medium.

In still another embodiment of the present invention, there is provided a process for microbial synthesis, wherein the nutrient mist medium further comprises a carbon source, a nitrogen source and an inorganic salt.

In another embodiment of the present invention, there is provided a process for microbial synthesis, wherein the mist conditioning agent is selected from group comprising of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4(1H)-quinolone, N-Hexanoyl-DL-homoserine lactone, N-[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone and a combination thereof. Norepinephrine, dopamine, alginate, polyglucosamine, colanic acid, cellulose, emulsan, chitosan, dextran, curdlan, kefiran, Lentinan, pullulan or a combination thereof.

In yet another embodiment of the present invention, there is provided a process for microbial synthesis, wherein the biofilm support material is selected from cotton, jute, hemp, manila, silk, linen, sisal, silica, acrylic, polyester, nylon, polypropylene, polyethylene, polytetrafluoroethylene, polymethylmethacrylate, polystyrene, polyvinyl chloride or a combination thereof.

In still another embodiment of the present invention, there is provided a process for microbial synthesis, wherein the obtained biofilm is having a thickness in the range of 50-250 μm.

In another aspect of the present invention, there is provided an apparatus for microbial synthesis, comprising of:
  (a) a mist generator and conditioning chamber comprising
    (i) a UV chamber; (ii) a sparger/inlet for sparging nitrogen gas or dry air; and (iii) a flow meter to control flow of gas;
  (b) a mist bioreactor comprising (i) an airtight reactor having perforated plates holding bio-film support equipped with a temperature controller to control temperature; (ii) an opening for light source for providing light of different wavelengths; (iii) a feed chamber/an opening for supply of gaseous feed intermittently or continuously; (iv) an opening for recycling feed gas from outlet to inlet chamber; (v) a provision to regulate mist particle size; and
  (c) a product collection and separation chamber.

These and other features, aspects, and advantages of the present subject matter will be better understood with reference to the following description. This summary is provided to introduce a selection of concepts in a simplified form.

BRIEF DESCRIPTION OF DRAWINGS

These and other features, aspects, and advantages of the present invention will become better understood when the following detailed description is read with reference to the accompanying drawings in which like characters represent like parts throughout the drawings wherein:

FIG. 3 illustrates (a) variation of titer and water utility in traditional fermentation and mist bioreactor; (b) variation of product titer with biofilm thickness; (c) the dependency between the ratio of mist and $N_2$ flow rate to the biofilm thickness

DETAILED DESCRIPTION OF THE INVENTION

For convenience, before further description of the present disclosure, certain terms employed in the specification, and examples are collected here. These definitions should be read in the light of the remainder of the disclosure and understood as by a person of skill in the art. The terms used herein have the meanings recognized and known to those of skill in the art, however, for convenience and completeness, particular terms and their meanings are set forth below.

Definition

For the purposes of this invention, the following terms will have the meaning as specified therein:

The articles "a", "an" and "the" are used to refer to one or to more than one (i.e., to at least one) of the grammatical object of the article.

The terms "comprise" and "comprising" are used in the inclusive, open sense, meaning that additional elements may be included. It is not intended to be construed as "consists of only".

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to" "including" and "including but not limited to" are used interchangeably.

The present invention relates to a microbial synthesis process having less/minimum water consumption and high product yield. Particularly, the present invention relates to a controlled use of ultra fine nutrient mist for the selective cultivation microbes in specially designed biofilm-bioreactor and uses the same in microbial synthesis. The process applies to the production of valuable products from both gaseous and liquid feed under strict aerobic/anaerobic or facultative conditions. Further, the process can have modulation of conditions to have a desired product profile i.e., supplying the substrate and nutrient mist to the mist bioreactor and manipulating stable biofilm formation by bacteriointerfacial self-assembly. Moreover, the process disclosed in the present invention provides a stable continuous method for obtaining high concentrated product without affecting the microbial viability and bioactivity. The improved mist-based bioreactor leads to significant savings in water and also allows for the design of photobioreactors of any desired shape. The present invention also allows for the use of a variety of types of feed materials for biosynthesis.

Thus, in accordance with the present invention, there is provided a process for microbial synthesis, the process comprising the steps of:
  (a) inoculating an electro active microbe in a nutrient mist medium in a mist generating and conditioning chamber;
  (b) adding a mist conditioning agent in the range of 50-70 ppm to the nutrient mist medium of step (a); mechanically mixing solutions of (a) and (b) in the chamber to form a homogeneous mixture and adding a bacterio-supramolecular self-assembly agent to the solution to obtain an ultra-fine mist;
(c) passing the obtained mist through a UV chamber for a duration of 2-5 seconds and sparging nitrogen gas or dry air to the mist in a mist bioreactor; wherein the ratio of mist and nitrogen gas is 1:2;
(d) layering the microbe on a biofilm support in the bioreactor to obtain a stable biofilm; passing controlled feed and collecting product in a product collection and separation chamber, wherein the microbe is added in the mist bioreactor along with a moisture indicator and ZnSe quantum dots in a concentration ranging from 100-500 nM.

In an embodiment of the present invention, there is provided a process of microbial synthesis, wherein the electro active microbe is selected from the group consisting of *Enterobacter aerogenes* MTCC 25016, *Serratia* sp. MTCC 25017, *Shewanella* sp. MTCC 25020 and *Alcaligenes* sp. MTCC 25022. The microbes were obtained from Indian Oil Corporation Limited (IOCL) Panipat Refinery, Panipat, Haryana, India.

In another embodiment of the present invention, there is provided a process of microbial synthesis, wherein the bacterio-supramolecular self-assembly agent is dioleoylphosphatydic acid.

In another embodiment of the present invention, there is provided a process for microbial synthesis, wherein the moisture indicator is selected from $CuCl_2$/silica Gel, porphyrin/$MgCl_2$/silica Gel, and Fe-hydroxy complexes/silica gel.

In the process of the present invention, any suitable mist medium may be used. Different formulations of medium can be used to produce biofilm of different types of microbes. The nutrient mist medium may be a complex, defined, or selective growth medium. More specifically, the nutrient medium defined can be a complex medium including, but not limited to complex dextrose based media, sea water media, domestic wastewater, municipal wastewater, industrial wastewater, surface runoff wastewater, soil extract media, or any natural water containing detectable amounts of phosphorus or nitrogen; or a defined medium, including, but not limited to Bristol's medium, Bolds Basal medium, Walne medium, Guillard's f medium, Blue-Green medium, D medium, DYTY medium, Jaworski's medium, K medium, MBL medium, Jorgensen's medium, and MLA medium; or a selective medium including, but not limited to minimal media based on specific nutrient auxotrophy, and selective media that incorporates antibiotics.

In another embodiment of the present invention, the nutrient mist medium is selected from complex dextrose based media, sea water media, domestic wastewater, municipal wastewater, industrial wastewater, surface runoff wastewater, soil extract media, or natural water; a defined medium, or a selective medium.

In another embodiment of the present invention, there is provided a process for microbial synthesis, wherein the nutrient mist medium further comprises a carbon source, a nitrogen source and an inorganic salt. The nutrient mist medium comprises a carbon source as alkane rich refinery feed stand and other conventional nutrients, such as a nitrogen source and an inorganic salt. The examples of suitable nitrogen sources include organic and inorganic nitrogen-containing compounds, such as peptone, urea, ammonium phosphate, ammonium chloride, ammonium sulfate and ammonium nitrate. Examples of the inorganic salts include phosphates, sulfates, and hydrochlorides of sodium, potassium, magnesium, iron, nickel, and zinc, such as $KH_2PO_4$, $K_2HPO_4$, $Na_2HPO_4 \cdot 12H_2O$, $MgSO_4 7H_2O$, $FeSO_4 JH_2O$, $ZnSO_4 JH_2O$, and NaCl. Moreover, other nutrients, such as yeast extract, meat extract, and D-biotin, can be added to the medium for assisting the growth of the yeast.

In still another embodiment of the present invention, there is provided a process for microbial synthesis, wherein the mist conditioning agent is selected from group comprising of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, cis-2-Dodecenoic acid, N-Heptanoyl-DL-homoserine lactone, 2-Heptyl-3-hydroxy-4(1H)-quinolone, N-Hexanoyl-DL-homoserine lactone, N-[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, cis-11-Methyl-2-dodecenoic acid, N-Octanoyl-DL-homoserine lactone, N-(3-Oxododecanoyl)-L-homoserine lactone, N-(3-Oxooctanoyl)-DL-homoserine lactone, N-(3-Oxooctanoyl)-L-homoserine lactone, N-(3-Oxotetradecanoyl)-L-homoserine lactone, N-Tetradecanoyl-DL-homoserine lactone and a combination thereof. Norepinephrine, dopamine, alginate, polyglucosamine, colanic acid, cellulose, emulsan, chitosan, dextran, curdlan, kefiran, Lentinan, pullulan and a combination thereof.

In yet another embodiment of the present invention, there is provided a process for microbial synthesis, wherein the biofilm support material in the mist bioreactor is selected from cotton, jute, hemp, manila, silk, linen, sisal, silica, acrylic, polyester, nylon, polypropylene, polyethylene, polytetrafluoroethylene, polymethylmethacrylate, polystyrene, polyvinyl chloride, and a combination thereof. In a preferred embodiment of the present invention, there is provided a process for microbial synthesis wherein the mist conditioning agent is N-Hexanoyl-DL-homoserine lactone. The biofilm conditioners to be supplied along with mist is in a concentration ranging from 50-100 ppm. The biofilm supports described herein can be of different shapes like honeycomb or layer-by-layer deposition. The pore diameter of the mist based biofilm supporter material may vary in size depending on the biofilm to be produced and the size of the bioreactor.

The average pore diameter biofilm support material can vary from 500 μm to 2500 μm. The pore size of the support should of at least 10 to 100 times of the average mist particle sizes.

In an embodiment of the present invention, the surface area of the biofilm support materials should be higher than 1.0 $m^2/g$.

In another embodiment of the present invention, the biofilm support material should be hydrophobic in nature. The surface area of the biofilm provides a mist to microorganism ratio such that the respiration of microorganisms is comparable in magnitude to microbial growth rate to maintain a stable biofilm.

In still another embodiment of the present invention, the biofilm can be stored at optimum conditions for more than 2-3 years with or without intermittent use.

In yet another embodiment of the present invention, there is provided a process for microbial synthesis, wherein the biofilm is having a thickness in the range of 50-250 μm. The biofilm thickness is dependent on the ratio between mist and nitrogen gas and can withstand a pH of 3-10.

In an aspect of the present invention, there is provided a process for generating ultra fine mist, the process comprising the steps of:
(a) selecting suitable nutrient rich mist media for any desired microbe;
(b) adding a mist conditioning agent in the range of 50-70 ppm;
(c) mechanical mixing of (a) and (b) in the mist-generating chamber to form a homogeneous mixture;
(d) adding bacterio-supramolecular self-assembler agent in the range of 2-5 ppm to the solution of step (c);
(e) sparging nitrogen gas or dry air having dew point ranging from −30 to −50° C. to the mixture in step (d) for a duration of 1-5 minutes to obtain an ultra fine mist; wherein the ultrafine mist is having water droplet size ranging from 50 to 250 µm;
(f) passing the obtained mist through a UV chamber for a duration of 2-5 seconds;
(g) regulating flow rate of the mist between 10-20 ml/min at the velocities below 3.0 m/s.
(h) sparging nitrogen gas along with mist so that the ratio between mist and nitrogen gas to be maintained as 2:1; and
(i) introducing the nitrogen gas sparged mist into the mist bioreactor.

In another aspect of the present invention, there is provided an apparatus for microbial synthesis comprising (1) a mist generator and conditioning chamber, (2) a mist bioreactor, and (3) at least a product collection and separation chamber.

In an embodiment of the present invention, an apparatus for microbial synthesis comprises of:
(a) a mist generator and conditioning chamber comprising (i) a UV chamber; (ii) a sparger/inlet for sparging nitrogen gas or dry air; and (iii) a flow meter to control flow of gas;
(b) a mist bioreactor comprising (i) an airtight reactor having perforated plates holding bio-film support equipped with a temperature controller to control temperature; (ii) an opening for light source for providing light of different wavelengths; (iii) a feed chamber/an opening for supply of gaseous feed intermittently or continuously; (iv) an opening for recycling feed gas from outlet to inlet chamber; (v) a provision to regulate mist particle size; and (c) a product collection and separation chamber.

The mist generation and conditioning chamber described herein is used for mist generation using ultra-sonication process. The ultrasonic field enhances the mixing of the media components and sterilization. The microbe is added in the nutrient mist medium and further, a reagent for bacterio-supramolecular self-assembler is added. Subsequently, the mist is passed through a UV chamber with an exposure time of 2-5 seconds. Furthermore, the mist should be stable for at least for 50-120 seconds. A nitrogen gas or dry air is sparged along with the mist to the mist bioreactor.

Figure 1:
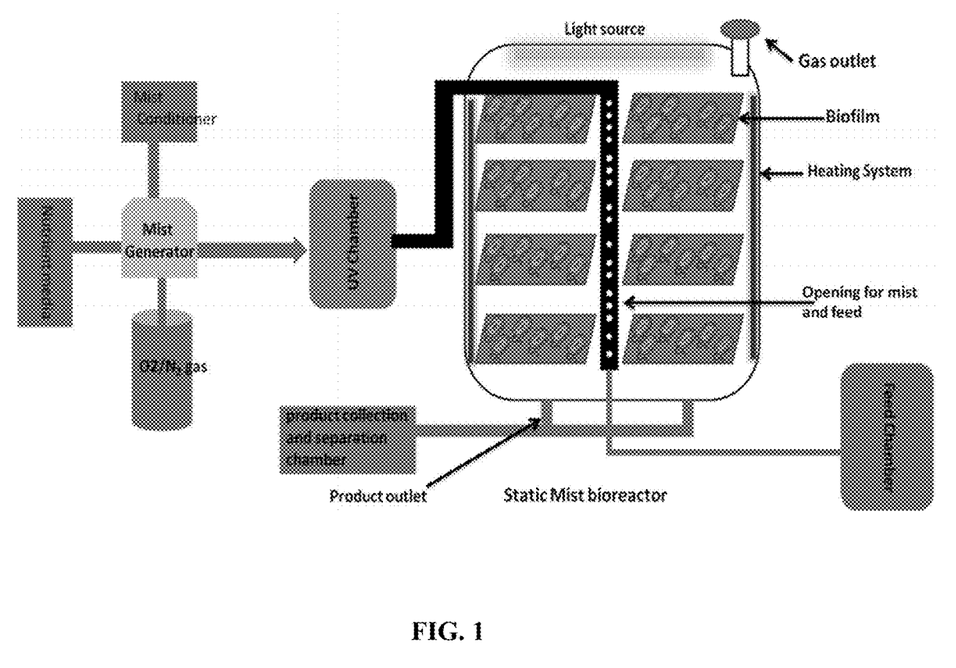
FIG. 1 illustrates the mist bioreactor in static mode configuration.
Figure 2:
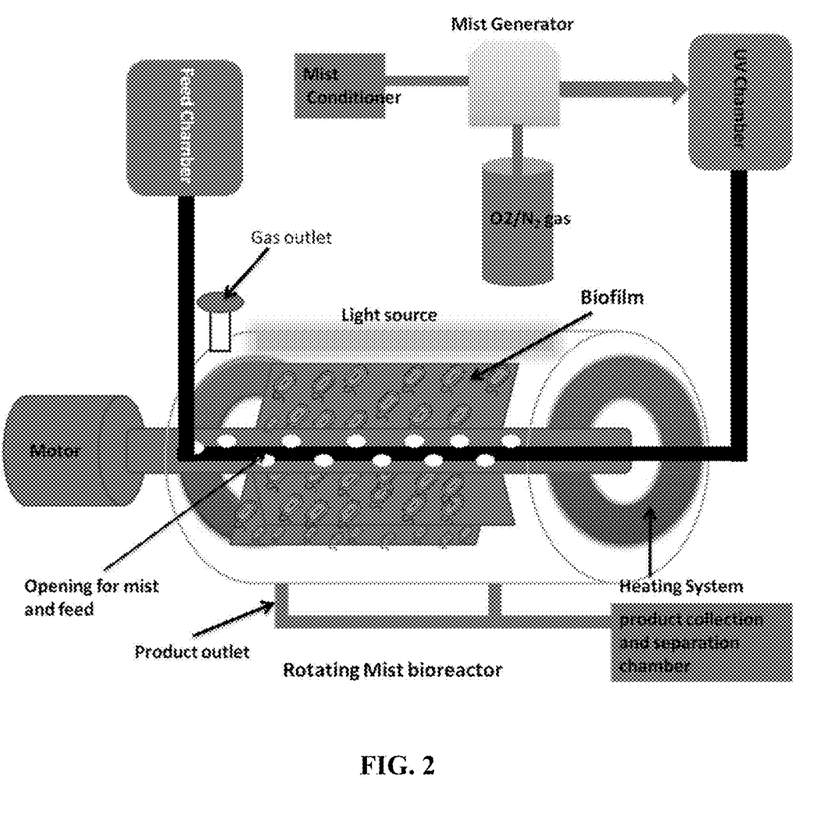
FIG. 2 illustrates the mist bioreactor in rotating mode configuration.

The mist bioreactor described herein can be configured to operate with either static or rotating biofilm. The static mist bioreactor comprises of an airtight reactor having arrangement of perforated plates at an angle of 45-55° against the axis for holding the biofilm supports. The number of perforated trays per reactor is in the range of 2 to 12, evenly distributed on the central axis along the radial direction of the central axis.

In rotating mist bioreactor, the bioreactor comprises of a cylindrical airtight reactor having porous axes at the center of the cylinder with the means to hold the trays that contain the biofilm supporter.

Further, the axis has pores for mist and feed transfer. The length of each perforated tray on the central axis is $\frac{1}{3}^{rd}$ or $\frac{1}{4}^{th}$ of the entire length of central axis. The gap between two perforated trays along the axial direction is 0.5 to 5.0 cm. The motor has a provision to rotate from 10-100 rpm.

The reactor is completely closed with provision for a complete anaerobic environment. The rotating mist bioreactor may also include a rotation device to rotate the axis containing the biofilm support and thereby rotationally exposing the biofilm to the nutrient mist, feed and light. hydro or wind forces and a mechanical attachment, such as a belt, chain, gear assembly, or combination thereof. The speed of rotation is between 1 to 100 rpm. The rotational device may further include a controller with optional sensors and/or timers to manually or automatically control the rotational rate of the bioreactor.

The mist bioreactor comprises an opening/inlet for feed wherein the feed gas may contain hydrogen, carbon dioxide and methane or any liquid. The biofilm in mist reactor is artificially illuminated by variously placed light emitting diodes which are controlled by a control mechanism based upon interaction with a plurality of sensors within the chamber. The present invention may also utilize natural sunlight or ambient light or combinations of ambient and directed light in order to obtain the desired effect. In one embodiment of the present invention, the mist bioreactor is completely artificially lighted and the emissions from the light emitting sources are coordinated by interaction between these light emitting sources preferably (light emitting diodes) having selected characteristics such as wavelength, frequency, intensity or other features and at least one sensor. In addition to the maintaining of optimal lighting conditions within the chamber, the temperature of the internal contents of the chamber can also be variously monitored and controlled to provide an optimal temperature for growth. Further, a heat sink is an integrated part of the cylindrical chamber.

The product collection and separation chamber described herein collects the products after the reaction. A separate opening is there for the product collection. High concentrated product is obtained through the product separation and further the product is purified by various techniques like crystallization, extractive distillation, and evaporation. The product selectivity by nano-photosensitized microbes can be controlled depending on the wavelength of light (400-700 nm).

Accordingly, the present method has many advantages such as: The process of the present invention is based on less water consumption and utilizes less quantity of water in the form of nutrient mist for a stable biofilm preparation. The media components used in the preparation of the nutrient mist does not require expensive sterilization process. The quantity of mist is highly regulated and controlled depending on the indicator in the biofilm. The supra-molecular self-assembly imposed by artificial lipid layer improves the feed and product tolerance with intact bioactivity. The concentrated product obtained in the process significantly lowers the separation and purification cost. Further, the product selectivity by photosensitized microbes can be tailored by light of different wave lengths. In addition, the appropriately designed mist bioreactor helps in proper mixing of feed and mist reactor in concurrent and countercurrent and the mist bioreactor has the provision for both static and rotating biofilm.

Although the subject matter has been described in considerable detail with reference to certain preferred embodiments thereof, other embodiments are possible.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods, the exemplary methods, devices and materials are described herein. It is to be understood that this disclosure is not limited to particular methods, and experimental conditions described, as such methods and conditions may vary.

Example 1: Microbial Synthesis of Alcohols from Carbon Dioxide in Mist Bioreactor Preparation of Bioreactor:

A 2.5 L (30 L×20 W×25 H inch) bioreactor was prepared with acrylic material with provision for mist and feed. Inside the bioreactor, there is provision for 8 no. of porous tray (10 L×5 W×3 H Inch) for holding the biofilm support material. The tray was placed 45-degree angle to the horizontal axis. Each tray was filled with polystyrene biofilm support material having surface area of 25 $m^2/g$. The whole reactor was placed in UV light for 30 minutes to sterilize it.

Seeding of inoculums: A pre grown inoculums containing 1:1 ratio of *Enterobacter aerogenes* MTCC 25016 and *Serratia* sp. MTCC 25017 having CFU 12*1011 was centrifuged and ~0.28 g of wet wt of the microbe was washed with 50 mM HEPES buffer and diluted with 8 ml of saline water having 125 nM concentrations of ZnSe quantum dots and 10 ppm of Erythrosine. Each tray of the reactor was equally sprayed with 1 ml of inoculum mixture.

Mist Generation and Conditioning:

The mist generation chamber consists of mist generation using ultra-sonication process. The ultrasonic field enhances the mixing of the media component. 2.5 g of $NaHCO_3$, 0.25 of $NH_4Cl$, 0.06 g of $NaH_2PO_4H_2O$, 0.1 g of KCl, 0.024 g of $C_6H_5FeO_7$ (ferric citrate), 10 ml of a vitamin mix and 10 ml of a trace mineral solution were prepared in 1 L of Deionized water. To the solution, 50-ppm N-Hexanoyl-DL-homoserine lactone was added as conditioning agent and 2-ppm of dioleoylphosphatydic acid was added as bacterio supramolecular self-assembler. The mixture was mechanically stirred for 30 minutes and then added to the mist generation chamber.

Figure 3:
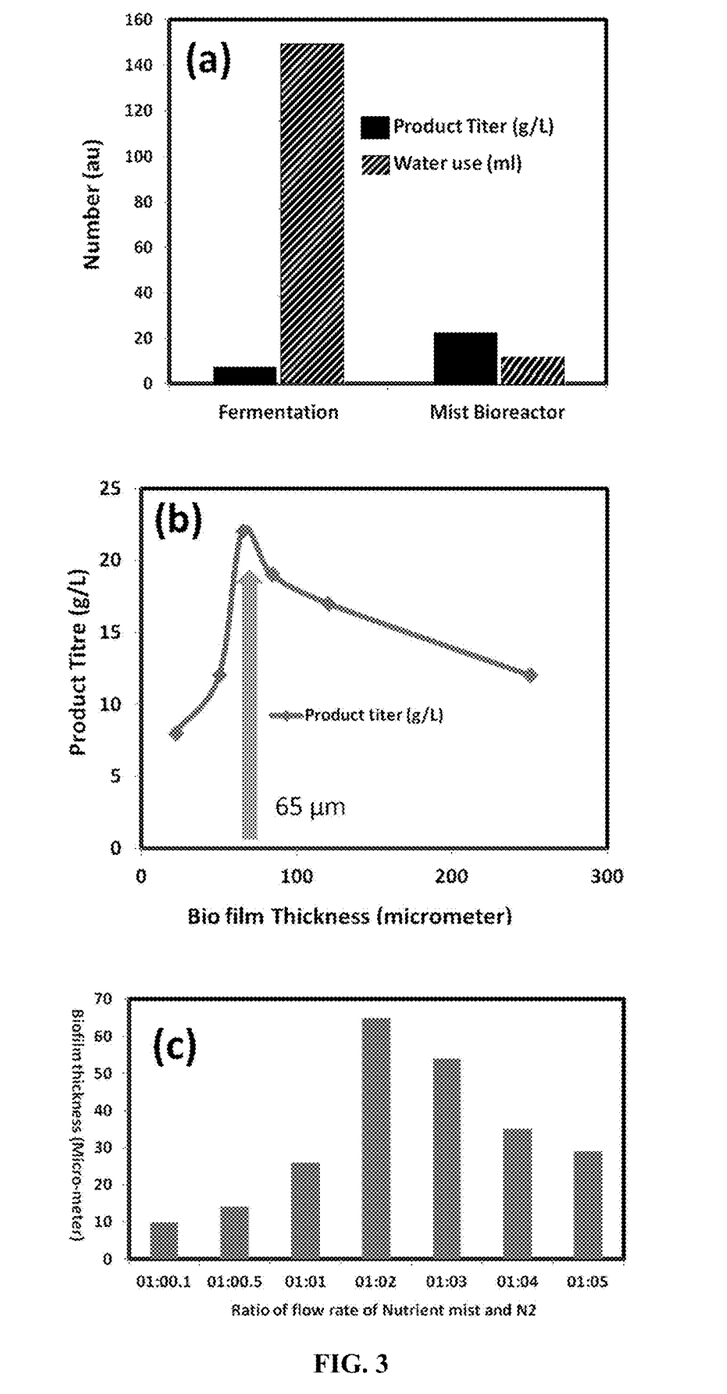

The mist was produced and passed through the UV chamber for 5 seconds at a flow rate of 10 ml/minute. At the same time, nitrogen gas was supplied to the chamber with 10 ml/min. The mixture of mist and nitrogen gas was supplied to the mist bioreactor. After 15 minutes of mist sparging, the reactor was stabilized for 6 hours at 37° C. After each 6 h interval mist was supplied to the chamber to initiate the biofilm preparation. After 74 hours, a stable biofilm of thickness ~62 μm was observed. After the stabilization of the biofilm, $CO_2$ (99.9%) was supplied through the feed section at a flow rate of 2 ml/min in a counter current mode. After each 1 h interval feed and mist was supplied at a ratio of 5:1 for 5 min. Visible light of wavelength (400-700 nm) was supplied in form of led light. After 24 hours of feed supply, the product droplets were collected from below the rector chamber. The product was found analyzed by GC and found to be mixture of ethanol and butanol. The product profile is depicted in FIG. 3.

Example 2: Comparing the Water Requirement/Consumption in the Mist Bioreactor Vs. in Traditional Fermentation To compare the amount of water needed in mist bioreactor and traditional fermentation, a controlled experiment was carried out using feed batch system. A fully-grown *Enterobacter aerogenes* MTCC 25016 and *Serratia* sp. MTCC 25017 (1:1) was prepared in 150 ml of water using the similar media composition as of the mist composition at 37° C. After 72 hours, the total titer obtained from $CO_2$ conversions were compared with that of mist based bioprocessing. As shown in the FIG. 3a, the total product titer in mist bioreactor was 3.1 times higher than that of fermentation with 13.6 times less water consumption. It was found that in the mist bioreactor, the titer was also highly dependent on the film thickness of the biofilm. A highest titer production observed at a biofilm thickness of 65 μm. Further, as shown in FIG. 3(c) the biofilm thickness is highly dependent on the ratio between the mist and nitrogen gas flow rate. An optimum thickness is obtained at a ratio of 1:2, which resulted in higher titer yield. Thus, these results demonstrate that process of the present invention is based on less water consumption and utilizes less quantity of water in the form of nutrient mist for a stable biofilm preparation.

What is claimed:

1. A process for microbial synthesis, the process comprising:
    diluting a pre grown inoculum with saline water having ZnSe quantum dots, and a silica gel mixture to prepare an inoculum mixture, wherein the pre grown inoculum comprises microbes, wherein the microbes are selected from the group consisting of *Enterobacter aerogenes* MTCC 25016, *Serratia* sp. MTCC 25017, *Shewanella* sp. MTCC 25020 and *Alcaligenes* sp. MTCC 25022;
    spraying the inoculum mixture on a biofilm support placed in a mist bioreactor to form a biofilm;
    adding a nutrient mist medium, a homoserine lactone, and dioleoylphosphatydic acid and mechanically stirring for about 30 minutes to form a homogeneous mixture;
    sending the homogeneous mixture to a mist generation chamber to form an ultra-fine mist, wherein the ultra-fine mist is formed by ultra sonication;
    passing the ultra-fine mist through a UV chamber for a duration of 2-5 seconds;
    sparging nitrogen gas along with the ultra-fine mist into the mist bioreactor; wherein the ratio of the ultra-fine mist and the nitrogen gas is 1:2;
    passing a feed through the mist bioreactor having the biofilm and collecting a product in a product collection and separation chamber.

2. The process as claimed in claim 1, wherein the silica gel mixture is selected from the group consisting of $CuCl_2$/silica gel, porphyrin/$MgCl_2$/silica gel, and Fe-hydroxy complexes/silica gel.

3. The process as claimed in claim 1, wherein the nutrient mist medium comprises $NaHCO_3$, $NH_4Cl$, $NaH_2PO_4H_2O$, KCl, $C_6H_5FeO_7$ (ferric citrate), a vitamin mix and a trace mineral solution in Deionized water.

4. The process as claimed in claim 1, wherein the homoserine lactone is selected from the group consisting of N-Butyryl-DL-homocysteine thiolactone, N-Butyryl-DL-homoserine lactone, N-(p-Coumaroyl)-L-homoserine lactone, N-Decanoyl-DL-homoserine lactone, N-Dodecanoyl-DL-homoserine lactone, N-Heptanoyl-DL-homoserine lactone, N-Hexanoyl-DL-homoserine lactone, N-[(RS)-3-Hydroxybutyryl]-L-homoserine lactone, N-(3-Hydroxydodecanoyl)-DL-homoserine lactone, N-(3-Hydroxytetradecanoyl)-DL-homoserine lactone, N-(β-Ketocaproyl)-L-homoserine lactone, N-(β-Ketocaproyl)-DL-homoserine lactone, N-Octanoyl-DL-homoserine lactone, N-(3-Oxododecanoyl)-L-homoserine lactone, N-(3-Oxooctanoyl)-DL-homoserine lactone, N-(β-Oxooctanoyl)-L-homoserine lactone, N-(3-Oxotetradecanoyl)-L-homoserine lactone, N-Tetradecanoyl-DL-homoserine lactone and a combination thereof.

5. The process as claimed in claim 1, wherein the biofilm support material is selected from the group consisting of cotton, jute, hemp, manila, silk, linen, sisal, silica, acrylic, polyester, nylon, polypropylene, polyethylene, polytetrafluroethylene, polymethylmethacrylate, polystyrene, polyvinyl chloride, and a combination thereof.

6. The process as claimed in claim 1, wherein the biofilm has a thickness in a range of 50-250 μm.

7. The process as claimed in claim 1, wherein the dioleoylphosphatydic acid is added in a range of 2-5 ppm to the homogeneous mixture.

8. The process as claimed in claim 1, wherein the dry air has dew point ranging from −30 to −50° C.

9. The process as claimed in claim 1, wherein the nitrogen gas or the dry air is sparged for a duration of 1-5 minutes to obtain the ultra-fine mist.

10. The process as claimed in claim 1, wherein the ultra-fine mist has a water droplet size ranging from 50 to 250 μm.

11. The process as claimed in claim 1, wherein the ultra-fine mist is sparged into the mist bioreactor at a flow rate between 10-20 ml/min and at a velocity below 3.0 m/s.

12. The process as claimed in claim 1, further comprising illuminating the biofilm.

13. The process as claimed in claim 12, wherein the biofilm is illuminated by natural sunlight, ambient light, or a combination of ambient and a directed light.

14. The process as claimed in claim 12, wherein the biofilm is artificially illuminated by light emitting diodes.

15. The process as claimed in claim 1, wherein the feed is 99.9% $CO_2$ and is passed through the mist bioreactor in a counter current mode.

16. The process as claimed in claim 1, wherein the product is a mixture of ethanol and butanol.

17. The process as claimed in claim 1, wherein the ZnSe quantum dots are in a concentration ranging from 100-500 nM.

* * * * *